(12) United States Patent
Takahashi

(10) Patent No.: US 10,689,358 B2
(45) Date of Patent: Jun. 23, 2020

(54) METHOD FOR PRODUCING INDAZOLE COMPOUND, AND INDAZOLE COMPOUND

(71) Applicant: FUJIFILM Corporation, Tokyo (JP)

(72) Inventor: Motomasa Takahashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/537,701

(22) Filed: Aug. 12, 2019

(65) Prior Publication Data

US 2019/0359590 A1 Nov. 28, 2019

Related U.S. Application Data

(63) Continuation of application No. PCT/JP2018/004996, filed on Feb. 14, 2018.

(30) Foreign Application Priority Data

Feb. 14, 2017 (JP) .................................. 2017-025255

(51) Int. Cl.
C07D 401/04 (2006.01)
C07D 231/56 (2006.01)

(52) U.S. Cl.
CPC ......... *C07D 401/04* (2013.01); *C07D 231/56* (2013.01)

(58) Field of Classification Search
CPC .......................... C07D 401/04; C07D 231/56
USPC ....................................................... 514/341
See application file for complete search history.

(56) References Cited

U.S. PATENT DOCUMENTS

| 7,776,890 B2 * | 8/2010 | Oinuma | C07D 231/56 514/338 |
|---|---|---|---|
| 2002/0082274 A1 | 6/2002 | Lambert et al. | |
| 2004/0127536 A1 | 7/2004 | Bhagwat et al. | |
| 2004/0171634 A1 | 9/2004 | Kania et al. | |
| 2005/0261339 A1 | 11/2005 | Ohi et al. | |
| 2006/0281789 A1 | 12/2006 | Shiotsu et al. | |
| 2011/0028390 A1 | 2/2011 | Corbett et al. | |
| 2016/0229809 A1 | 8/2016 | Hutchinson et al. | |
| 2018/0222886 A1 | 9/2018 | Chen et al. | |
| 2018/0297948 A1 | 10/2018 | Kim et al. | |

FOREIGN PATENT DOCUMENTS

| EP | 1 510 516 A1 | 3/2005 |
|---|---|---|
| EP | 1 650 194 A1 | 4/2006 |
| EP | 3 333 157 A1 | 6/2018 |
| JP | 2003-503481 A | 1/2003 |
| JP | 2004-514706 A | 5/2004 |
| JP | 2006-523721 A | 10/2006 |
| JP | 2011-521939 A | 7/2011 |
| JP | 2016-530210 A | 9/2016 |
| WO | 01/02369 A2 | 1/2001 |
| WO | 03/101968 A1 | 12/2003 |
| WO | 2004/094388 A2 | 11/2004 |
| WO | 2005/012258 A1 | 2/2005 |
| WO | 2005/094823 A1 | 10/2005 |
| WO | 2009/144554 A1 | 12/2009 |
| WO | 2016/129933 A2 | 8/2016 |
| WO | 2017/024968 A1 | 2/2017 |

OTHER PUBLICATIONS

Laufer et al., "The Discovery of PLK4 Inhibitors: (E)-3-((1H-Indazol-6-yl)methylene)indolin-2-ones as Novel Antiproliferative Agents" Journal of Medicinal Chemistry, 2013, vol. 56, No. 15, pp. 6069-6087.

Sampson et al., "The Discovery of Polo-Like Kinase 4 Inhibitors: Design and Optimization of Spiro[cyclopropane-1,3'[3H]indol]-2'(1'H)-ones as Orally Bioavailable Antitumor Agents" Journal of Medicinal Chemistry, 2015, vol. 58, No. 1, pp. 130-146.

Norris, et al., "Heavy-Metal-Free Reduction Methodology for Large-Scale Synthesis Applicable to Heterocyclic and Arylhydrazines", Organic Process Research & Development, 2009, vol. 13, No. 2, pp. 354-357.

Chekal, et al., "Development of an Efficient Pd-Catalyzed Coupling Process for Axitinib", Organic Process Research & Development, vol. 18, 2014, pp. 266-274.

International Search Report dated May 15, 2018 from the International Searching Authority in counterpart International Application No. PCT/JP2018/004996.

(Continued)

*Primary Examiner* — Kristin A Vajda

(74) *Attorney, Agent, or Firm* — Sughrue Mion, PLLC

(57) ABSTRACT

An object of the invention is to provide a novel method for producing an indazole compound, by which an indazole compound can be produced without using a reaction reagent that exhibits strong toxicity, and a novel indazole compound. According to the invention, a method for producing an indazole compound, including obtaining an indazole compound or a salt thereof from a diazonium salt prepared from an aniline compound in the presence of a compound represented by the following General Formula (1), is provided.

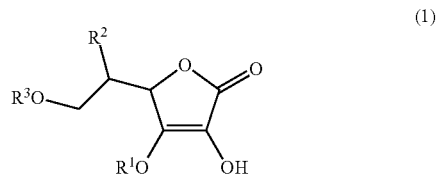

(1)

In the formula, $R^1$ represents a hydrogen atom or an alkali metal; $R^2$ represents a hydrogen atom, a hydroxyl group, or the like; and $R^3$ represents a hydrogen atom, a $C_{1-30}$ alkylcarbonyl group which may have a substituent, or a $C_{6-20}$ arylcarbonyl group which may have a substituent.

12 Claims, No Drawings

(56) References Cited

OTHER PUBLICATIONS

International Preliminary Report on Patentability dated Aug. 20, 2019 from the International Bureau in counterpart International Application No. PCT/JP2018/004996.
Written Opinion dated May 15, 2018 from the International Bureau in counterpart International Application No. PCT/JP2018/004996.
Extended European Search Report dated Nov. 11, 2019, from the European Patent Office in counterpart European Application No. 18754591.8.

\* cited by examiner

METHOD FOR PRODUCING INDAZOLE COMPOUND, AND INDAZOLE COMPOUND

CROSS-REFERENCE TO RELATED APPLICATIONS

This application is a Continuation of PCT International Application No. PCT/JP2018/004996 filed on Feb. 14, 2018, which claims priority under 35 U.S.C. § 119(a) to Japanese Patent Application No. 2017-025255 filed on Feb. 14, 2017. Each of the above application(s) is hereby expressly incorporated by reference, in its entirety, into the present application.

BACKGROUND OF THE INVENTION

1. Field of the Invention

The present invention relates to a method for producing an indazole compound that is useful as a synthetic intermediate of a medicinal drug, an agrochemical, or a functional material, and to an indazole compound.

2. Description of the Related Art

An indazole compound may be used as a synthetic intermediate of a medicinal drug, an agrochemical, or a functional material. For example, axitinib, which is used as a therapeutic drug for renal cell carcinoma, is produced using an indazole compound as a synthetic intermediate (Org. Process Res. & Dev. 2014, 266-274).

Regarding a method of synthesizing an indazole compound, several methods are known. For example, in WO2009/144554A, a method of synthesizing an indazole compound from a 2'-aminoacetophenone derivative is described. In JP2016-530210A, it is described that an indazole compound is synthesized by condensing nitrobenzaldehyde and malonic acid, and then performing reductive cyclization using hydrazine and Raney nickel. Furthermore, in JP2004-514706A and Org. Process Res. & Dev. 2009, 354-357, methods of obtaining oxalic acid hydrazide by reducing a diazonium salt prepared from an aniline derivative with ascorbic acid are described. Oxalic acid hydrazide is derived into free hydrazine by acid hydrolysis.

SUMMARY OF THE INVENTION

In regard to the method for synthesizing an indazole compound described in WO2009/144554A, tin dichloride is used as a reaction reagent. Tin dichloride exhibits strong environmental toxicity and has a problem that a residue derived from the tin reagent remains on the target object after a reaction. In the method for synthesizing an indazole compound described in JP2016-530210A, the range of applicable compounds is significantly limited.

An object of the invention is to provide a novel production method for an indazole compound, by which an indazole compound can be produced without using a reaction reagent that exhibits strong toxicity. Another object of the invention is to provide a novel indazole compound.

The inventors of the present invention repeatedly conducted thorough investigations on the problems described above, and as a result, the inventors found that an indazole compound can be produced with high yield by obtaining an indazole compound from a diazonium salt prepared from a predetermined aniline compound in the presence of a compound represented by General Formula (1) that is described in the present specification. Thus, the inventors completed the invention.

That is, according to the invention, the following inventions are provided.

<1> A method for producing an indazole compound, comprising obtaining an indazole compound represented by the following General Formula (3) or a salt thereof from a diazonium salt prepared from an aniline compound represented by the following General Formula (2) in the presence of a compound represented by the following General Formula (1),

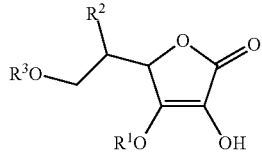

(1)

in the formula, $R^1$ represents a hydrogen atom or an alkali metal;

$R^2$ represents a hydrogen atom, a hydroxyl group, an amino group, a mercapto group, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{1-6}$ alkoxy group which may have a substituent, a $C_{6-20}$ aryloxy group which may have a substituent, a $C_{1-6}$ alkylamino group which may have a substituent, a $C_{6-20}$ arylamino group which may have a substituent, a $C_{1-6}$ alkylthio group which may have a substituent, a $C_{6-20}$ arylthio group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent; and $R^3$ represents a hydrogen atom, a $C_{1-30}$ alkylcarbonyl group which may have a substituent, or a $C_{6-20}$ arylcarbonyl group which may have a substituent,

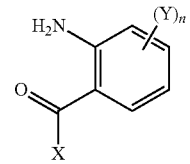

(2)

in the formula,

X represents a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{2-6}$ alkenyl group which may have a substituent, a $C_{2-6}$ alkynyl group which may have a substituent, a $C_{6-20}$ aryl group which may have a substituent, or a heterocyclic group which may have a substituent;

Y's each independently represent a halogen atom, a carboxyl group, a hydroxyl group, an amino group, a mercapto group, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{1-6}$ alkoxy group which may have a substituent, a $C_{6-20}$ aryloxy group which may have a substituent, a $C_{1-6}$ alkylamino group which may have a substituent, a $C_{6-20}$ acylamino group which may have a substituent, a $C_{1-6}$ alkylthio group which may have a substituent, a $C_{6-20}$ arylthio group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent; and n is an integer from 0 to 4; and in a case in which n is 2 or greater, a plurality of existing Y's may be identical with or different from one another, and

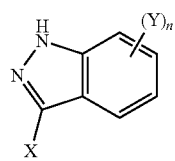

(3)

in the formula, X, Y, and n have the same meanings as those described above.

<2> The method for producing an indazole compound according to <1>, wherein the aniline compound represented by General Formula (2) is a compound represented by the following General Formula (4), and the indazole compound represented by General Formula (3) is a compound represented by the following General Formula (5),

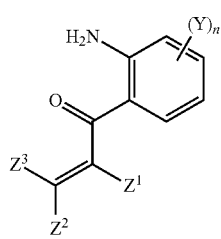

(4)

in the formula, $Z^1$ to $Z^3$ each independently represent a hydrogen atom, a $C_{1-6}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, a $C_{3-8}$ cycloalkenyl group which may have a substituent, a $C_{6-20}$ aryl group which may have a substituent, or a heterocyclic group which may have a substituent;

$Z^1$ and $Z^2$ may be bonded together to form a ring; and

Y and n have the same meanings as those described above, and

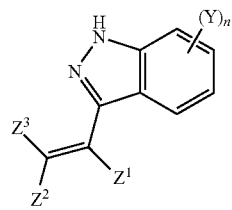

(5)

in the formula, $Z^1$ to $Z^3$, Y, and n have the same meanings as those described above.

<3> The method for producing an indazole compound according to <1> or <2>, wherein the aniline compound represented by General Formula (2) is a compound represented by the following General Formula (6), and the indazole compound represented by General Formula (3) is a compound represented by the following General Formula (7),

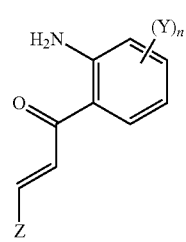

(6)

in the formula,

Z represents a hydrogen atom, a $C_{1-6}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, a $C_{3-8}$ cycloalkenyl group which may have a substituent, a $C_{6-20}$ aryl group which may have a substituent, or a heterocyclic group which may have a substituent; and Y and n have the same meanings as those described above, and

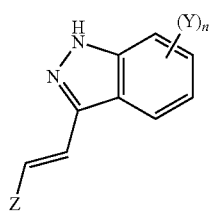

(7)

in the formula, Z, Y, and n have the same meanings as those described above.

<4> The method for producing an indazole compound according to <3>, wherein Z is a group represented by the following General Formula (8),

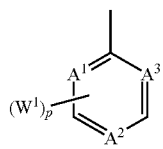

(8)

in the formula, $W^1$ represents a halogen atom, a cyano group, a nitro group, an amino group, a formyl group, a carboxyl group, a sulfo group, a hydroxyl group, a $C_{1-6}$ alkylcarbonyl group which may have a substituent, a $C_{6-20}$ arylcarbonyl group which may have a substituent, a $C_{1-6}$ alkylsulfonyl group which may have a substituent, a $C_{6-20}$ arylsulfonyl group which may have a substituent, a $C_{1-6}$ alkylsulfinyl group which may have a substituent, a $C_{6-20}$ arylsulfinyl group which may have a substituent, a $C_{1-6}$ alkylamino group which may have a substituent, a $C_{6-20}$ arylamino group which may have a substituent, a $C_{1-6}$ alkoxy group which may have a substituent, a $C_{6-20}$ aryloxy group which may have a substituent, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent;

$A^1$ to $A^3$ each independently represent —$CR^4$— or —N—;

$R^4$ represents a hydrogen atom or $W^1$;

p is an integer from 0 to 5; in a case in which p is 2 or greater, a plurality of existing $W^1$'s may be identical with or different from one another; and two or more $W^1$'s may be bonded together to form a fused ring together with a benzene ring.

<5> The method for producing an indazole compound according to <4>, wherein $W^1$ represents a halogen atom, a cyano group, a nitro group, a formyl group, a carboxyl group, a sulfo group, a $C_{1-6}$ alkylcarbonyl group which may have a substituent, a $C_{6-20}$ arylcarbonyl group which may have a substituent, a $C_{1-6}$ alkylsulfonyl group which may have a substituent, a $C_{6-20}$ arylsulfonyl group which may have a substituent, a $C_{1-6}$ alkylsulfinyl group which may have a substituent, or a $C_{6-20}$ arylsulfinyl group which may have a substituent; and p is 1.

<6> The method for producing an indazole compound according to any one of <1> to <5>, wherein the diazonium salt prepared from the aniline compound is a diazonium salt obtained by causing nitrite to act on the aniline compound under acidic conditions.

<7> The method for producing an indazole compound according to any one of <1> to <6>, wherein a solvent used in the process of obtaining the diazonium salt is a mixed solvent including acetic acid and water.

<8> The method for producing an indazole compound according to any one of <1> to <7>, wherein Y represents a halogen atom, a mercapto group, a $C_{1-6}$ alkylthio group which may have a substituent, a $C_{1-6}$ alkyl group which may have a substituent, a $C_{1-6}$ alkoxy group which may have a substituent, a carboxyl group, a $C_{3-8}$ cycloalkenyl group which may have a substituent, a $C_{6-20}$ aryl group which may have a substituent, or a heterocyclic group which may have a substituent.

<9> The method for producing an indazole compound according to any one of <1> to <8>, wherein Y represents a halogen atom, a $C_{3-8}$ cycloalkenyl group which may have a substituent, a $C_{6-20}$ aryl group which may have a substituent, or a heterocyclic group which may have a substituent.

<10> The method for producing an indazole compound according to any one of <1> to <9>, wherein $R^2$ represents a hydroxyl group.

<11> The method for producing an indazole compound according to any one of <1> to <10>, wherein the compound represented by General Formula (1) is a compound represented by the following General Formula (10),

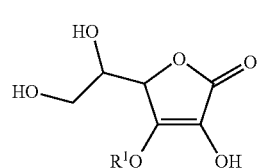

(10)

in the formula, $R^1$ has the same meaning as that described above.

<12> The method for producing an indazole compound according to any one of <1> to <11>, wherein the compound represented by General Formula (1) is a compound represented by the following General Formula (11).

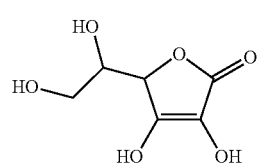

(11)

<13> An indazole compound represented by the following General Formula (12) or a salt thereof,

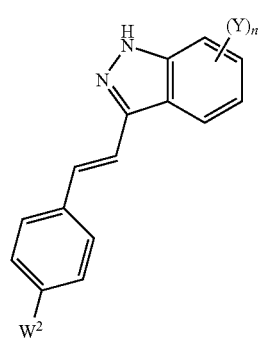

(12)

in the formula, $W^2$ represents a halogen atom, a cyano group, a nitro group, a formyl group, a carboxyl group, a sulfo group, a $C_{1-6}$ alkylcarbonyl group which may have a substituent, a $C_{6-20}$ arylcarbonyl group which may have a substituent, a $C_{1-6}$ alkylsulfonyl group which may have a substituent, a $C_{6-20}$ arylsulfonyl group which may have a substituent, a $C_{1-6}$ alkylsulfinyl group which may have a substituent, or a $C_{6-20}$ arylsulfinyl group which may have a substituent;

Y's each independently represent a halogen atom, a carboxyl group, a hydroxyl group, an amino group, a mercapto group, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{1-6}$ alkoxy group which may have a substituent, a $C_{6-20}$ aryloxy group which may have a substituent, a $C_{1-6}$ alkylamino group which may have a substituent, a $C_{6-20}$ acylamino group which may have a substituent, a $C_{1-6}$ alkylthio group which may have a substituent, a $C_{6-20}$ arylthio group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent; and n is an integer from 0 to 4; and in a case in which n is 2 or greater, a plurality of existing Y's may be identical with or different from one another, provided that in a case in which $W^2$ is a formyl group, n is an integer from 1 to 4.

<14> The indazole compound or a salt thereof according to <13>, wherein the indazole compound represented by General Formula (12) is a compound represented by the following General Formula (13),

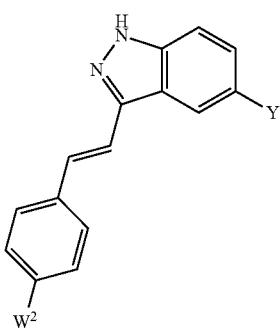

(13)

in the formula, $W^2$ represents a cyano group; and Y represents a halogen atom.

<15> An indazole compound represented by the following General Formula (14) or a salt thereof,

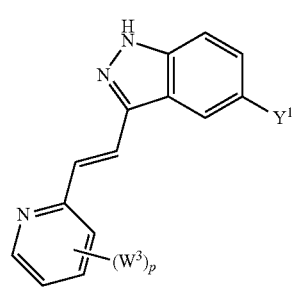

(14)

in the formula, $W^3$ represents a halogen atom, a cyano group, a nitro group, an amino group, a formyl group, a carboxyl group, a sulfo group, a hydroxyl group, a $C_{1-6}$ alkylcarbonyl group which may have a substituent, a $C_{6-20}$ arylcarbonyl group which may have a substituent, a $C_{1-6}$ alkylsulfonyl group which may have a substituent, a $C_{6-20}$ arylsulfonyl group which may have a substituent, a $C_{1-6}$ alkylsulfinyl group which may have a substituent, a $C_{6-20}$ arylsulfinyl group which may have a substituent, a $C_{1-6}$ alkylamino group which may have a substituent, a $C_{6-20}$ arylamino group which may have a substituent, a $C_{1-6}$ alkoxy group which may have a substituent, a $C_{6-20}$ aryloxy group which may have a substituent, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent;

$Y^1$ represents a halogen atom, a carboxyl group, a hydroxyl group, an amino group, a mercapto group, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{1-6}$ alkoxy group which may have a substituent, a $C_{6-20}$ aryloxy group which may have a substituent, a $C_{1-6}$ alkylamino group which may have a substituent, a $C_{6-20}$ arylamino group which may have a substituent, a $C_{1-6}$ alkylthio group which may have a substituent, a $C_{6-20}$ arylthio group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent; and p is an integer from 0 to 4; and in a case in which p is 2 or greater, a plurality of existing $W^3$'s may be identical with or different from one another.

<16> The indazole compound or a salt thereof according to <15>, wherein the indazole compound represented by General Formula (14) is a compound represented by the following General Formula (15),

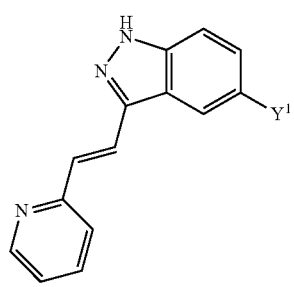

(15)

in the formula, $Y^1$ represents a halogen atom.

According to the method of the invention, an indazole compound that is useful as a synthetic intermediate of a medicinal drug, an agrochemical, or a functional material can be produced without using a reaction reagent which exhibits strong toxicity, such as tin dichloride. The indazole compound of the invention is useful as a synthetic intermediate of a medicinal drug, an agrochemical, or a functional material.

DESCRIPTION OF THE PREFERRED EMBODIMENTS

The invention, will be described in detail below.

According to the invention, unless particularly stated otherwise, percentage (%) is % by mass.

According to the invention, unless particularly stated otherwise, various terms have the following meanings.

An alkali metal is Li, Na, K, Rb, Cs, or Fr, and is preferably Li, Na, or K.

A halogen atom means a fluorine atom, a chlorine atom, a bromine atom, or an iodine atom.

A $C_{1-6}$ alkyl group means a linear or branched $C_{1-6}$ alkyl group such as a methyl, ethyl, propyl, isopropyl, n-butyl, sec-butyl, isobutyl, tert-butyl, pentyl, isopentyl, 2-methylbutyl, 2-pentyl, 3-pentyl, or hexyl group.

A $C_{3-8}$ cycloalkyl group means a $C_{3-8}$ cycloalkyl group such as a cyclopropyl, cyclobutyl, cyclopentyl, cyclohexyl, or cycloheptyl group.

A $C_{1-6}$ alkoxy-$C_{1-6}$ alkyl group means a $C_{1-6}$ alkyloxy-$C_{1-6}$ alkyl group such as a methoxymethyl or 1-ethoxyethyl group.

A $C_{6-20}$ aryl-$C_{1-6}$ alkyl group means a $C_{6-20}$ aryl-$C_{1-6}$ alkyl group (an aralkyl group in which the alkyl moiety is a $C_{1-6}$ alkyl), such as a benzyl, diphenylmethyl, trityl, phenethyl, 2-phenylpropyl, 3-phenylpropyl, or naphthylmethyl group.

A $C_{1-6}$ alkoxy group means a linear, cyclic, or branched $C_{1-6}$ alkyloxy group such as a methoxy, ethoxy, propoxy, isopropoxy, cyclopropoxy, butoxy, isobutoxy, sec-butoxy, tert-butoxy, cyclobutoxy, pentyloxy, or hexyloxy group.

A $C_{6-20}$ aryloxy group means a $C_{6-20}$ aryloxy group such as a phenoxy or naphthyloxy group.

A $C_{1-6}$ alkylamino group means a linear or branched $C_{1-6}$ alkylamino group such as a methylamino, ethylamino, propylamino, isopropylamino, butylamino, sec-butylamino, tert-butylamino, pentylamino, or hexylamino group.

A $C_{6-20}$ arylamino group means a $C_{6-20}$ arylamino group such as a phenylamino, p-tolylamino, or 2-naphthylamino group.

A $C_{1-6}$ alkylthio group means a linear or branched $C_{1-6}$ alkylthio group such as a methylthio, ethylthio, propylthio, isopropylthio, butylthio, sec-butylthio, isobutylthio, tert-butylthio, pentylthio, isopentylthio, 2-methylbutylthio, 2-pentylthio, 3-pentylthio, or hexylthio group.

A $C_{6-20}$ arylthio group means a $C_{6-20}$ arylthio group such as a phenylthio or 2-naphthylthio group.

A $C_{2-6}$ alkenyl group means a linear or branched $C_{2-6}$ alkenyl group such as a vinyl, allyl, propenyl, isopropenyl, butenyl, isobutenyl, 1,3-butadienyl, pentenyl, or hexenyl group.

A $C_{3-8}$ cycloalkenyl group means a $C_{3-8}$ cycloalkenyl group such as a cyclopropenyl, cyclobutenyl, cyclopentenyl, or cyclohexenyl group.

A $C_{2-6}$ alkynyl group means a linear or branched $C_{2-6}$ alkynyl group such as an ethynyl, propynyl, butynyl, pentynyl, or hexynyl group.

A $C_{1-6}$ alkylcarbonyl group means a $C_{1-6}$ alkylcarbonyl group such as an acetyl, propionyl, butyryl, isobutyryl, or pivaloyl group. The expression $C_{1-6}$ in the "$C_{1-6}$ alkylcarbonyl group" means that the number of carbon atoms of the alkyl moiety is 1 to 6.

A $C_{1-30}$ alkylcarbonyl group means a $C_{1-30}$ alkylcarbonyl group such as an acetyl, propionyl, butyryl, isobutyryl, pivaloyl, or palmitoyl group. The expression $C_{1-30}$ in the "$C_{1-30}$ alkylcarbonyl group" means that the number of carbon atoms of the alkyl moiety is 1 to 30.

A $C_{6-20}$ arylcarbonyl group means an arylcarbonyl group in which the number of carbon atoms of the aryl moiety of benzoyl or the like is 6 to 20.

A $C_{1-6}$ alkylsulfonyl group means a $C_{1-6}$ alkylsulfonyl group such as a methylsulfonyl, ethylsulfonyl, or propylsulfonyl group.

A $C_{6-20}$ arylsulfonyl group means a $C_{6-20}$ arylsulfonyl group such as a benzenesulfonyl, p-toluenesulfonyl, or naphthalenesulfonyl group.

A $C_{1-6}$ alkylsulfinyl group means a $C_{1-6}$ alkylsulfinyl group such as a methylsulfinyl, ethylsulfinyl, or propylsulfinyl group.

A $C_{6-20}$ arylsulfinyl group means a $C_{6-20}$ arylsulfinyl group such as a benzenesulfinyl, p-toluenesulfinyl, or naphthalenesulfinyl group.

A $C_{6-20}$ aryl group means an aryl group having 6 to 20 carbon atoms, such as a phenyl or naphthyl group.

A monocyclic nitrogen-containing heterocyclic group means a monocyclic nitrogen-containing heterocyclic group containing a heteroatom that forms the ring of an aziridinyl, azetidinyl, pyrrolidinyl, pyrrolinyl, pyrrolyl, piperidyl, tetrahydropyridyl, dihydropyridyl, pyridyl, homopiperidinyl, octahydroazocinyl, imidazolidinyl, imidazolinyl, imidazolyl, pyrazolidinyl, pyrazolinyl, pyrazolyl, piperadinyl, diazepanyl, pyrazinyl, pyridazinyl, pyrimidinyl, homopiperazinyl, triazolyl, or tetrazolyl group, and also containing a monocyclic nitrogen-containing heteroaryl.

The monocyclic oxygen-containing heterocyclic group means a monocyclic oxygen-containing heterocyclic group containing only an oxygen atom as a heteroatom that forms the ring of an oxetanyl, tetrahydrofuranyl, furanyl, tetrahydropyranyl, pyranyl, 1,3-dioxanyl, or 1,4-dioxanyl group.

A monocyclic sulfur-containing heterocyclic group means a thienyl group, tetrahydrothiopyranyl, 1,1-dioxidotetrahydrothiopyranyl, or the like.

A monocyclic nitrogen/oxygen-containing heterocyclic group means a monocyclic nitrogen/oxygen-containing heterocyclic group containing only a nitrogen atom and an oxygen atom as heteroatoms that form the ring of an oxazolyl, isoxazolyl, oxadiazolyl, morpholinyl, or oxazepanyl group.

A monocyclic nitrogen/sulfur-containing heterocyclic group means a monocyclic nitrogen/sulfur-containing heterocyclic group containing only a nitrogen atom and a sulfur atom as heteroatoms that form the ring of a thiazolyl, isothiazolyl, thiadiazolyl, thiomorpholinyl, 1-oxidothiomorpholinyl, or 1,1-dioxidothiomorpholinyl group.

A monocyclic heterocyclic group means a monocyclic nitrogen-containing heterocyclic group, a monocyclic oxygen-containing heterocyclic group, a monocyclic sulfur-containing heterocyclic group, a monocyclic nitrogen/oxygen-containing heterocyclic group, or a monocyclic nitrogen/sulfur-containing heterocyclic group.

A bicyclic nitrogen-containing heterocyclic group means a bicyclic nitrogen-containing heterocyclic group containing only a nitrogen atom as a heteroatom that forms the ring of an indolinyl, indolyl, isoindolinyl, isoindolyl, benzimidazolyl, indazolyl, benzotriazolyl, pyrazolopyridinyl, quinolyl, tetrahydroquinolinyl, quinolyl, tetrahydroisoquinolinyl, isoquinolinyl, quinolidinyl, cinnolinyl, phthalazinyl, quinazolinyl, dihydroquinoxalinyl, quinoxalinyl, naphthyridinyl, purinyl, pteridiny, or quinuclidinyl group.

A bicyclic oxygen-containing heterocyclic group means a bicyclic oxygen-containing heterocyclic group containing only an oxygen atom as a heteroatom that forms the ring of a 2,3-dihydrobenzofuranyl, benzofuranyl, isobenzofuranyl, chromanyl, chromenyl, isochromanyl, 1,3-benzodioxolyl, 1,3-benzodioxanyl, or 1,4-benzodioxanyl group.

A bicyclic sulfur-containing heterocyclic group means a bicyclic sulfur-containing heterocyclic group containing only a sulfur atom as a heteroatom that forms the ring of a 2,3-dihydrobenzothienyl or a benzothienyl group.

A bicyclic nitrogen/oxygen-containing heterocyclic group means a bicyclic nitrogen/oxygen-containing heterocyclic group containing only a nitrogen atom and an oxygen atom as heteroatoms that form the ring of a benzoxazolyl, benzisoxazolyl, benzoxadiazolyl, benzomorpholinyl, dihydropyranopyridyl, dioxolopyridyl, furopyridinyl, dihydrodioxinopyridyl, or dihydropyridoxazinyl group.

A bicyclic nitrogen/sulfur-containing heterocyclic group means a bicyclic nitrogen/sulfur-containing heterocyclic group containing a nitrogen atom and a sulfur atom as heteroatoms that form the ring of a benzothiazolyl, benzisothiazolyl, or benzothiadiazolyl group.

A bicyclic heterocyclic group means a bicyclic nitrogen-containing heterocyclic group, a bicyclic oxygen-containing heterocyclic group, a bicyclic sulfur-containing heterocyclic group, a bicyclic nitrogen/oxygen-containing heterocyclic group, or a bicyclic nitrogen/sulfur-containing heterocyclic group.

A spiro-type heterocyclic group means a spiro-type heterocyclic group containing one or more of a nitrogen atom, an oxygen atom, or a sulfur atom as heteroatoms that form the ring of a 2,6-diazaspiro[3.3]heptyl, 2,7-diazaspiro[3.5]nonyl, 2-oxa-6-azaspiro[3.3]heptyl, 1,4-dioxaspiro[4.5]decyl, 1-oxa-8-azaspiro[4.5]decyl, or 1-thia-8-azaspiro[4.5]decyl group.

A bridge type heterocyclic group means a bridge type heterocyclic group which contains one or more nitrogen atoms and may further contain one or more of an oxygen atom or a sulfur atom, as heteroatoms that form the ring of a 3-oxa-8-azabicyclo[3.2.1]octyl, 8-oxa-3-azabicyclo[3.2.1]octyl, or quinuclidinyl group.

A heterocyclic group means a monocyclic heterocyclic group, a bicyclic heterocyclic group, a spiro-type heterocyclic group, or a bridge type heterocyclic group.

Examples of the substituent for a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{1-6}$ alkoxy group which may have a substituent, a $C_{6-20}$ aryloxy group which may have a substituent, a $C_{1-6}$ alkylamino group which may have a substituent, a $C_{6-20}$ arylamino group which may have a substituent, a $C_{1-6}$ alkylthio group which may have a substituent, a $C_{6-20}$ arylthio group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, a heterocyclic group which may have a substituent, a $C_{1-30}$ alkylcarbonyl group which may have a substituent, a $C_{6-20}$ arylcarbonyl group which may have a substituent, a $C_{1-6}$ alkylcarbonyl group which may have a substituent, a $C_{6-20}$ arylcarbonyl group which may have a substituent, a $C_{1-6}$ alkylsulfonyl group which may have a substituent, a $C_{6-20}$ arylsulfonyl group which may have a substituent, a $C_{1-6}$ alkylsulfinyl group which may have a substituent, and a $C_{6-20}$ arylsulfinyl group which may have a substituent, include a halogen atom, a cyano group, a nitro group, a formyl group, a carboxyl group, a sulfo group, a hydroxyl group, an amino group, a mercapto group, a $C_{1-6}$ alkyl group, a $C_{3-8}$ cycloalkyl group, a $C_{1-6}$ alkoxy-$C_{1-6}$ alkyl group, a $C_{6-20}$ aryl-$C_{1-6}$ alkyl group, a $C_{1-6}$ alkoxy group, a $C_{6-20}$ aryloxy group, a $C_{1-6}$ alkylamino group, a $C_{6-20}$ arylamino group, a $C_{1-6}$ alkylthio group, a $C_{6-20}$ arylthio group, a $C_{2-6}$ alkenyl group, a $C_{3-8}$ cycloalkenyl group, a $C_{2-6}$ alkynyl group, a $C_{6-20}$ aryl group, a heterocyclic group, a $C_{1-30}$ alkylcarbonyl group, a $C_{6-20}$ arylcarbonyl group, a $C_{1-6}$ alkylsulfonyl group, a $C_{6-20}$ arylsulfonyl group, a $C_{1-6}$ alkylsulfinyl group, and a $C_{6-20}$ arylsulfinyl group.

The production method according to the embodiment of the invention will be explained.

The method for producing an indazole compound according to the embodiment of the invention is a method including obtaining an indazole compound represented by General Formula (3) or a salt thereof

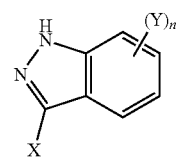

(3)

(in the formula, X, Y, and n have the same meanings as those described above)

from a diazonium salt prepared from an aniline compound represented by General Formula (2)

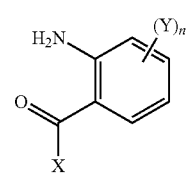

(2)

(in the formula,

X represents a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{2-6}$ alkenyl group which may have a substituent, a $C_{2-6}$ alkynyl group which may have a substituent, a $C_{6-20}$ aryl group which may have a substituent, or a heterocyclic group which may have a substituent;

Y's each independently represent a halogen atom, a carboxyl group, a hydroxyl group, an amino group, a mercapto group, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{1-6}$ alkoxy group which may have a substituent, a $C_{6-20}$ aryloxy group which may have a substituent, a $C_{1-6}$ alkylamino group which may have substituent, a $C_{6-20}$ arylamino group which may have a substituent, a $C_{1-6}$ alkylthio group which may have a substituent, a $C_{6-20}$ arylthio group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent; and n is an integer from 0 to 4; and in a case in which n is 2 or greater, a plurality of existing Y's may be identical with or different from one another), in the presence of a compound represented by General Formula (1)

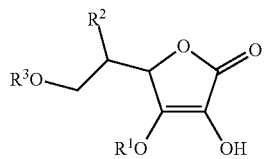

(in the formula, $R^1$ represents a hydrogen atom or an alkali metal;

$R^2$ represents a hydrogen atom, a hydroxyl group, an amino group, a mercapto group, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{1-6}$ alkoxy group which may have a substituent, a $C_{6-20}$ aryloxy group which may have a substituent, a $C_{1-6}$ alkylamino group which may have a substituent, a $C_{6-20}$ arylamino group which may have a substituent, a $C_{1-6}$ alkylthio group which may have a substituent, a $C_{6-20}$ arylthio group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent; and $R^3$ represents a hydrogen atom, a $C_{1-30}$ alkylcarbonyl group which may have a substituent, or a $C_{6-20}$ arylcarbonyl group which may have a substituent).

$R^1$ is preferably a hydrogen atom or a sodium atom, and more preferably a hydrogen atom.

$R^2$ is preferably a hydroxyl group.

$R^3$ is preferably a hydrogen atom or a $C_{1-30}$ alkylcarbonyl group which may have a substituent, and more preferably a hydrogen atom.

X is preferably a $C_{1-6}$ alkyl group which may have a substituent, a $C_{3-8}$ cycloalkyl group which may have a substituent, a $C_{2-6}$ alkenyl group which may have a substituent, or a $C_{2-6}$ alkynyl group which may have a substituent, and more preferably a $C_{2-6}$ alkenyl group which may have a substituent.

Y is preferably a halogen atom, a carboxyl group, a mercapto group, a $C_{1-6}$ alkyl group which may have a substituent, a $C_{1-6}$ alkoxy group which may have a substituent, a $C_{1-6}$ alkylthio group which may have a substituent, a $C_{3-8}$ cycloalkenyl group which may have a substituent, a $C_{6-20}$ aryl group which may have a substituent, or a heterocyclic group which may have a substituent; more preferably a halogen atom, a $C_{3-8}$ cycloalkenyl group which may have a substituent, a $C_{6-20}$ aryl group which may have a substituent, or a heterocyclic group which may have a substituent; and even more preferably a halogen atom. A bromine atom is most preferred.

n is preferably 1.

Preferably, the aniline compound represented by General Formula (2) is a compound represented by General Formula (4)

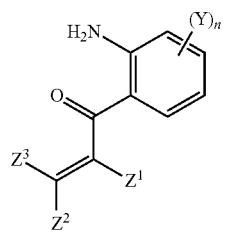

(in the formula, $Z^1$ to $Z^3$ each independently represent a hydrogen atom, a $C_{1-6}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, a $C_{3-8}$ cycloalkenyl group which may have a substituent, a $C_{6-20}$ aryl group which may have a substituent, or a heterocyclic group which may have a substituent;

$Z^1$ and $Z^2$ may be bonded together to form a ring; and

Y and n have the same meanings as those described above), and the indazole compound represented by General Formula (3) is a compound represented by General Formula (5)

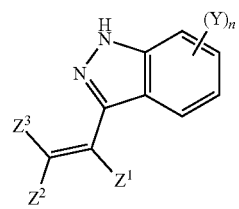

(in the formula, $Z^1$ to $Z^3$, Y, and n have the same meanings as those described above).

Preferred ranges of Y and n are the same as described above.

$Z^1$ to $Z^3$ are each independently preferably a hydrogen atom, a $C_{1-6}$ alkyl group which may have a substituent, a $C_{2-6}$ alkenyl group which may have a substituent, a $C_{2-6}$ alkynyl group which may have a substituent, a $C_{6-20}$ aryl group which may have a substituent, or a heterocyclic group which may have a substituent; more preferably a hydrogen atom, a $C_{6-20}$ aryl group which may have a substituent, or a heterocyclic group which may have a substituent; and even more preferably a hydrogen atom or a $C_{6-20}$ aryl group which may have a substituent.

The ring formed by $Z^1$ and $Z^2$ bonded together is not particularly limited; however, the ring is preferably a 5-membered ring or a 6-membered ring; more preferably a 6-membered ring; and even more preferably a cyclohexene ring or a benzene ring. A benzene ring is most preferred.

Preferably, the aniline compound represented by General Formula (2) is a compound represented by General Formula (6)

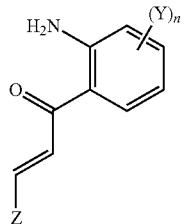

(6)

(in the formula, Z represents a hydrogen atom, a $C_{1-6}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, a $C_{3-8}$ cycloalkenyl group which may have a substituent, a $C_{6-20}$ aryl group which may have a substituent, or a heterocyclic group which may have a substituent; and Y and n have the same meanings as those described above), and the indazole compound represented by General Formula (3) is a compound represented by General Formula (7)

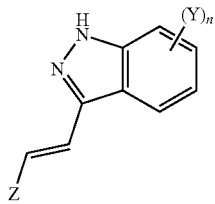

(7)

(in the formula, Z, Y, and n have the same meanings as those described above.

Preferred ranges of Y and n are the same as described above.

A preferred range of Z is the same as the preferred range of $Z^1$ to $Z^3$).

Preferably, Z is a group represented by General Formula (8).

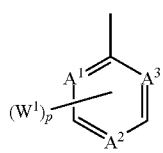

(8)

(In the formula, $W^1$ represents a halogen atom, a cyano group, a nitro group, an amino group, a formyl group, a carboxyl group, a sulfo group, a hydroxyl group, a $C_{1-6}$ alkylcarbonyl group which may have a substituent, a $C_{6-20}$ arylcarbonyl group which may have a substituent, a $C_{1-6}$ alkylsulfonyl group which may have a substituent, a $C_{6-20}$ arylsulfonyl group which may have a substituent, a $C_{1-6}$ alkylsulfinyl group which may have a substituent, a $C_{6-20}$ arylsulfinyl group which may have a substituent, a $C_{1-6}$ alkylamino group which may have a substituent, a $C_{6-20}$ arylamino group which may have a substituent, a $C_{1-6}$ alkoxy group which may have a substituent, a $C_{6-20}$ aryloxy group which may have a substituent, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent; $A^1$ to $A^3$ each independently represent —$CR^4$— or —N—;

$R^4$ represents a hydrogen atom or $W^1$; p is an integer from 0 to 5; in a case in which p is 2 or greater, a plurality of existing $W^1$'s may be identical with or different from one another; and two or more $W^1$'s may be bonded together to form a fused ring together with a benzene ring.)

In General Formula (8), $W^1$ is preferably a halogen atom, a cyano group, a nitro group, a formyl group, a carboxyl group, a sulfo group, a $C_{1-6}$ alkylcarbonyl group which may have a substituent, a $C_{6-20}$ arylcarbonyl group which may have a substituent, a $C_{1-6}$ alkylsulfonyl group which may have a substituent, a $C_{6-20}$ arylsulfonyl group which may have a substituent, a $C_{1-6}$ alkylsulfinyl group which may have a substituent, a $C_{6-20}$ arylsulfinyl group which may have a substituent, and a cyano group is most preferred. As $W^1$ is an electron-withdrawing group as described above, it is possible to produce a compound represented by General Formula (3) with higher yield.

In General Formula (8), it is more preferable that p is 1.

It is preferable that Y is a halogen atom, a mercapto group, a $C_{1-6}$ alkylthio group which may have a substituent, a $C_{1-6}$ alkyl group which may have a substituent, a $C_{1-6}$ alkoxy group which may have a substituent, a carboxyl group, a $C_{3-8}$ cycloalkenyl group which may have a substituent, a $C_{6-20}$ aryl group which may have a substituent, or a heterocyclic group which may have a substituent.

It is more preferable that Y is a halogen atom, a $C_{3-8}$ cycloalkenyl group which may have a substituent, a $C_{6-20}$ aryl group which may have a substituent, or a heterocyclic group which may have a substituent.

In regard to the production method according to the embodiment of the invention, the compound represented by General Formula (3) can be produced by reducing a compound represented by General Formula (2A). The compound represented by General Formula (2A) can be produced from a compound represented by General Formula (2). This process is represented by the following reaction formula.

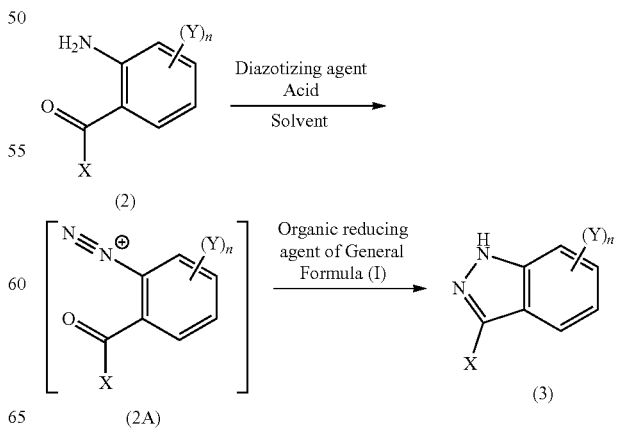

In the formula, X, Y, and n are as defined in the present specification.

A compound represented by General Formula (3) can be produced by reacting a compound represented by General Formula (2) with an acid and a diazotizing agent in a solvent, thereby preparing an intermediate represented by General Formula (2A), and then treating the intermediate with an organic reducing agent represented by General Formula (1).

Examples of the solvent include a carboxylic acid, a nitrile, an ether, and water, and these solvents may be used as mixtures.

Examples of the carboxylic acid include formic acid, acetic acid, propionic acid, and trifluoroacetic acid.

Examples of the nitrile include acetonitrile and propionitrile.

Examples of the ether include diethyl ether, diisopropyl ether, dioxane, tetrahydrofuran, anisole, ethylene glycol dimethyl ether, diethylene glycol dimethyl ether, and diethylene glycol diethyl ether.

The solvent is more preferably a mixture including a carboxylic acid (for example, acetic acid) and water; even more preferably a mixed solvent including acetic acid and water; and particularly preferably a mixed solvent of acetic acid and water. The volume ratio of acetic acid and water in a mixed solvent including acetic acid and water (or a mixed solvent of acetic acid and water) is not particularly limited; however, the volume ratio is preferably 5:1 to 1:1, more preferably 4:1 to 1:1, and even more preferably 3:1 to 1:1.

The amount of use of the solvent is not particularly limited; however, the amount of use is desirably a 1-fold to 10-fold amount (v/w), preferably a 1-fold to 5-fold amount (v/w), and more preferably a 1-fold to 3-fold amount, with respect to the compound represented by General Formula (2). v/w represents volume/mass.

The diazotizing agent is more preferably nitrous acid or a nitrite (for example, sodium nitrite).

The amount of use of the diazotizing agent is desirably a 1-fold to 2-fold molar amount, preferably a 1-fold to 1.5-fold molar amount, and more preferably a 1-fold to 1.2-fold molar amount, with respect to the compound represented by General Formula (2).

It is preferable that the diazonium salt prepared from an aniline compound is a diazonium salt obtained by causing nitrite to act on an aniline compound under acidic conditions.

Regarding the acid used at the time of producing a diazonium salt, hydrochloric acid, sulfuric acid, or the like can be used.

The amount of use of the acid is desirably a 1-fold to 5-fold molar amount, preferably a 2-fold to 5-fold molar amount, and more preferably a 2-fold to 4-fold molar amount, with respect to the compound represented by General Formula (2).

According to the invention, a compound represented by General Formula (1) is used as an organic reducing agent.

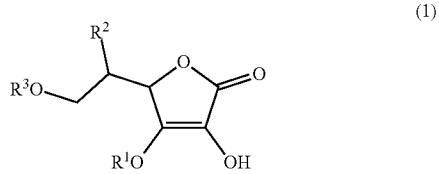

(1)

In General Formula (1), $R^1$, $R^2$, and $R^3$ are as defined in the present specification.

In General Formula (1), preferred ranges of $Z^1$ to $Z^3$ are the same as described above.

Regarding the compound represented by General Formula (1), a compound represented by General Formula (10) is preferred

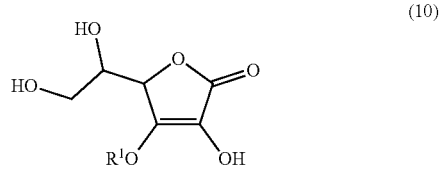

(10)

(in the formula, $R^1$ represents a hydrogen atom or an alkali metal), and a compound represented by General Formula (11) is more preferred.

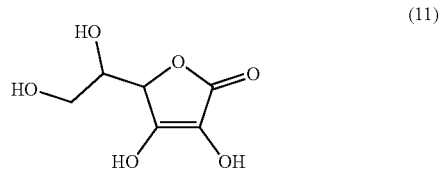

(11)

Specific examples of the compound represented by General Formula (1) include ascorbic acid, isoascorbic acid, sodium ascorbate, and an ascorbic acid ester, and ascorbic acid and sodium ascorbate are preferred.

According to the invention, it has been found that as an organic reducing agent that is safe and has sufficient reactivity, a compound represented by General Formula (1) can be used. By using a compound represented by General Formula (1) as the organic reducing agent, a satisfactory yield can be achieved. Meanwhile, the yield of the method for synthesizing an indazole compound as described in WO2009/144554A is 64%, which is not sufficient, and it is also not suitable to say that the yield of the method for synthesizing an indazole compound as described in JP2016-530210A is sufficiently high.

The amount of use of the compound represented by General Formula (1) is desirably a 1-fold to 5-fold molar amount, preferably a 1-fold to 2.5-fold molar amount, and more preferably a 1.1-fold to 1.3-fold molar amount, with respect to the compound represented by General Formula (2).

In regard to the process of preparing an intermediate represented by General Formula (2A), the reaction temperature is desirably −50° C. to 20° C., preferably −35° C. to 10° C., and more preferably −15° C. to 5° C.

In regard to the process of preparing an intermediate represented by General Formula (2A), the reaction time is desirably 10 minutes to 4 hours, preferably 10 minutes to 2 hours, and more preferably 30 minutes to 1 hour.

After an intermediate represented by General Formula (2A) is prepared, urea is added to the reaction liquid mixture to remove any excess diazotizing agent (nitric acid, nitrite, or the like), and then the intermediate may be treated with an organic reducing agent represented by General Formula (1).

In regard to the process of reducing an intermediate represented by General Formula (2A) and thereby obtaining a compound represented by General Formula (3), the reaction temperature is desirably 0° C. to 80° C., preferably 40° C. to 80° C., and more preferably 60° C. to 80° C.

In regard to the process of reducing an intermediate represented by General Formula (2A) and thereby obtaining a compound represented by General Formula (3), the reaction time is desirably 10 minutes to 8 hours, preferably 10 minutes to 4 hours, and more preferably 30 minutes to 2 hours.

A compound represented by General Formula (3), which is obtained by the production method described above, can be isolated and purified by conventional methods such as extraction, crystallization, distillation, or column chromatography. Furthermore, the compound represented by General Formula (3) obtained according to the production method described above may also be used directly in the subsequent reaction without being isolated.

In regard to the compounds used for the production method described above, in a case in which there are isomers (for example, an enantiomer, a geometric isomer, or a tautomer), these isomers can also be used. Furthermore, in a case in which solvates, hydrates, and crystals of various shapes exist, these solvates, hydrates, and crystals of various shapes can also be used. In regard to the compounds used in the production method described above, any compound having a substituent (for example, an amino group, a hydroxyl group, or a carboxyl group) that can be protected can have such a group protected in advance with a conventional protective group, and after the reaction, such a protective group can be eliminated by a method that is known per se. With regard to the protective group, Greene's Protective Groups in Organic Synthesis, 5$^{th}$ Edition can be referred to.

A compound obtained by the production method described above or a salt thereof can be derived into another compound or a salt thereof by subjecting the compound to reactions that are known per se, such as, for example, condensation, addition, oxidation, reduction, rearrangement, substitution, halogenation, dehydration, or hydrolysis, or by combining those reactions as appropriate.

Furthermore, according to the invention, a novel indazole compound is provided.

According to a first aspect, the indazole compound according to the embodiment of the invention is an indazole compound represented by the following General Formula (12) or a salt thereof.

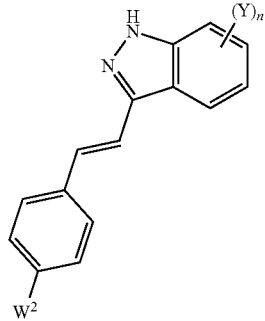

(12)

(In the formula, $W^2$ represents a halogen atom, a cyano group, a nitro group, a formyl group, a carboxyl group, a sulfo group, a $C_{1-6}$ alkylcarbonyl group which may have a substituent, a $C_{6-20}$ arylcarbonyl group which may have a substituent, a $C_{1-6}$ alkylsulfonyl group which may have a substituent, a $C_{6-20}$ arylsulfonyl group which may have a substituent, a $C_{1-6}$ alkylsulfinyl group which may have a substituent, or a $C_{6-20}$ arylsulfinyl group which may have a substituent;

Y's each independently represent a halogen atom, a carboxyl group, a hydroxyl group, an amino group, a mercapto group, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{1-6}$ alkoxy group which may have a substituent, a $C_{6-20}$ aryloxy group which may have a substituent, a $C_{1-6}$ alkylamino group which may have a substituent, a $C_{6-20}$ arylamino group which may have a substituent, a $C_{1-6}$ alkylthio group which may have a substituent, a $C_{6-20}$ arylthio group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent, n is an integer from 0 to 4; and in a case in which n is 2 or greater, a plurality of existing Y's may be identical with or different from one another, provided that in a case in which $W^2$ is a formyl group, n is an integer from 1 to 4.)

Preferred ranges of Y and n are the same as described above.

$W^2$ is preferably a cyano group.

$W^2$ is preferably a cyano group.

Y's are preferably each independently a halogen atom, a carboxyl group, a mercapto group, a $C_{1-6}$ alkyl group which may have a substituent, a $C_{1-6}$ alkoxy group which may have a substituent, a $C_{1-6}$ alkylthio group which may have a substituent, a $C_{3-8}$ cycloalkenyl group which may have a substituent, a $C_{6-20}$ aryl group which may have a substituent, or a heterocyclic group which may have a substituent. Y's are more preferably each independently a halogen atom, a $C_{3-8}$ cycloalkenyl group which may have a substituent, a $C_{6-20}$ aryl group which may have a substituent, or a heterocyclic group which may have a substituent.

Y's are even more preferably each independently a halogen atom, and a bromine atom is most preferred.

n is preferably 1.

An example of the indazole compound represented by General Formula (12) may be a compound represented by General Formula (13).

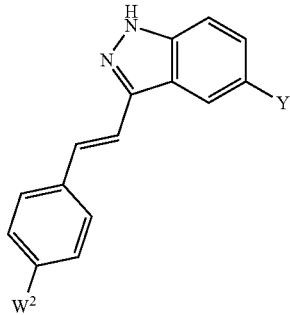

(13)

(In the formula, $W^2$ represents a cyano group; and Y represents a bromine atom.)

According to a second aspect, the indazole compound according to the embodiment of the invention is an indazole compound represented by the following General Formula (14) or a salt thereof.

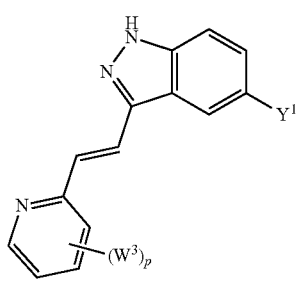

(14)

(In the formula, $W^3$ represents a halogen atom, a cyano group, a nitro group, an amino group, a formyl group, a carboxyl group, a sulfo group, a hydroxyl group, a $C_{1-6}$ alkylcarbonyl group which may have a substituent, a $C_{6-20}$ arylcarbonyl group which may have a substituent, a $C_{1-6}$ alkylsulfonyl group which may have a substituent, a $C_{6-20}$ arylsulfonyl group which may have a substituent, a $C_{1-6}$ alkylsulfinyl group which may have a substituent, a $C_{6-20}$ arylsulfinyl group which may have a substituent, a $C_{1-6}$ alkylamino group which may have a substituent, a $C_{6-20}$ arylamino group which may have a substituent, a $C_{1-6}$ alkoxy group which may have a substituent, a $C_{6-20}$ aryloxy group which may have a substituent, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent; and $Y^1$ represents a halogen atom, a carboxyl group, a hydroxyl group, an amino group, a mercapto group, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{1-6}$ alkoxy group which may have a substituent, a $C_{6-20}$ aryloxy group which may have a substituent, a $C_{1-6}$ alkylamino group which may have a substituent, a $C_{6-20}$ arylamino group which may have a substituent, a $C_{1-6}$ alkylthio group which may have a substituent, a $C_{6-20}$ arylthio group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent; p is an integer from 0 to 4; and in a case in which p is 2 or greater, a plurality of existing $W^3$'s may be identical with or different from one another.)

$Y^1$ is preferably a halogen atom, a carboxyl group, a mercapto group, a $C_{1-6}$ alkyl group which may have a substituent, a $C_{1-6}$ alkoxy group which may have a substituent, a $C_{1-6}$ alkylthio group which may have a substituent, a $C_{3-8}$ cycloalkenyl group which may have a substituent, a $C_{6-20}$ aryl group which may have a substituent, or a heterocyclic group which may have a substituent.

$Y^1$ is more preferably a halogen atom, a $C_{3-8}$ cycloalkenyl group which may have a substituent, a $C_{6-20}$ aryl group which may have a substituent, or a heterocyclic group which may have a substituent.

$Y^1$ is even more preferably a halogen atom, and a bromine atom is most preferred.

$W^3$ is preferably a halogen atom, a cyano group, a nitro group, a formyl group, a carboxyl group, a sulfo group, a $C_{1-6}$ alkylcarbonyl group which may have a substituent, a $C_{6-20}$ arylcarbonyl group which may have a substituent, a $C_{1-6}$ alkylsulfonyl group which may have a substituent, a $C_{6-20}$ arylsulfonyl group which may have a substituent, a $C_{1-6}$ alkylsulfinyl group which may have a substituent, or a $C_{6-20}$ arylsulfinyl group which may have a substituent; and more preferably a cyano group or a hydrogen atom. A hydrogen atom is most preferred.

p is preferably 0.

An example of the indazole compound represented by General Formula (14) may be a compound represented by General Formula (15).

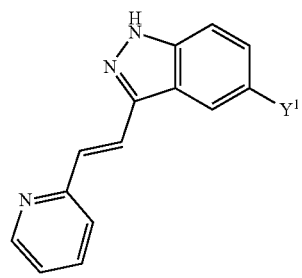

(15)

(In the formula, $Y^1$ represents a bromine atom.)

Examples of a salt of the indazole compound include salts for basic groups such as an amino group; and acidic groups such as a hydroxyl group and a carboxyl group, which are conventionally known.

In a case in which simply an indazole compound is mentioned in the present specification, a salt of the indazole compound is also included.

Examples of salts for basic groups include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid.

Examples of salts for acidic groups include salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

With regard to the indazole compound or a salt thereof, in a case in which isomers (for example, an enantiomer and a geometric isomer) exist, the invention includes those isomers and also include solvates, hydrates, and crystals of various shapes.

EXAMPLES

Hereinafter, the invention will be described by way of Examples, Comparative Examples, and Reference Examples; however, the invention is not intended to be limited to these.

Medium-pressure preparative column chromatography was performed using Smart FLASH EPCLC-W-Prep 2XY (Yamazen, Inc.).

The mixing ratio for an eluent is a volume ratio. For example, "ethyl acetate/hexane=1:1→ethyl acetate/hexane 4:1" means that an eluent of 50% by mass of ethyl acetate/50% by mass of hexane was changed finally to an eluent of 80% by mass of ethyl acetate/20% by mass of hexane.

A $^1$H-NMR spectrum was measured using tetramethylsilane as an internal standard and using Bruker AV400N (Bruker Corporation), and all of δ values were expressed in ppm.

A high performance liquid chromatography mass analysis was measured using AQUITY UPLC H-Class System (Waters Corporation). Hereinafter, this will be abbreviated to UPLC-MS.

Reference Example 1

Synthesis Method for (E)-4(3-(2-amino-5-bromophenyl)-3-oxoprop-1-en-1-yl)benzonitrile

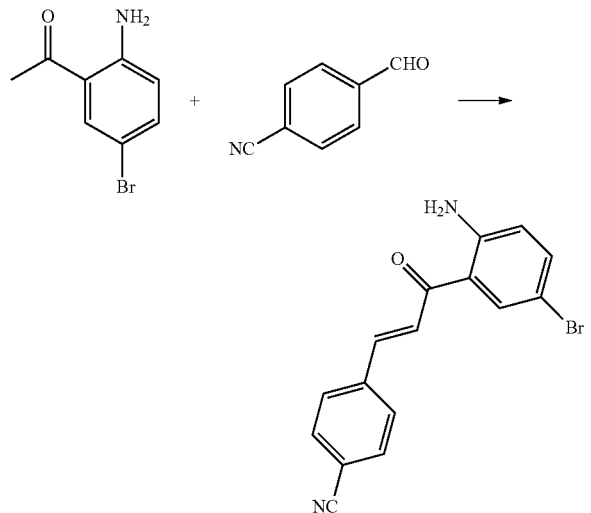

333 g of 1-(2-amino-5-bromophenyl)ethan-1-one, 12.4 g of sodium hydroxide, 1,330 mL of ethanol, and 300 mL of water were mixed, and the temperature was increased to 40° C. Subsequently, 204 g of 4-formylbenzonitrile was added thereto in five divided portions over 20 minutes. After the mixture was stirred for 30 minutes, the reaction liquid was added to 1 L of water, and thereby the reaction liquid was cooled to room temperature. The mixture was stirred for one hour, and then crystals were suction filtered using a 150-mm Nutsche filter. The crystals were washed continuously with 3.7 L of water and then dried for 17 hours in a fan dryer at 60° C. Subsequently, (E)-4(3-(2-amino-5-bromophenyl)-3-oxoprop-1-en-1-yl)benzonitrile was obtained.

$^1$H-NMR (CDCl$_3$) δ value: 6.41 (2H, broad-s), 6.63 (1H, d, J=8.8 Hz), 7.38 (1H, dd, J=2.0 Hz, 8.8 Hz), 7.59 (1H, d, J=15.6 Hz), 7.71 (1H, d, 15.6 Hz), 7.72 (4H, s), 7.90 (1H, d, 2.0 Hz) ppm.

Reference Example 2

Synthesis Method for (E)-1-(2-amino-5-bromophenyl)-3-(pyridin-2-yl)prop-2-en-1-one

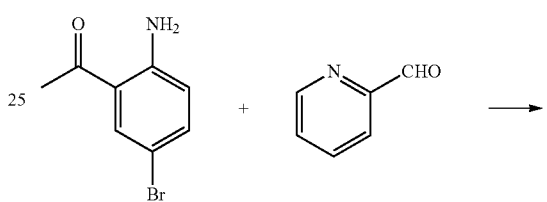

2.0 g of 1-(2-amino-5-bromophenyl)ethan-1-one, 0.07 g of sodium hydroxide, 8 mL of ethanol, and 2 mL of water were mixed, the temperature was raised to 40° C., and then 0.89 mL of pyridine-2-carboxyaldehyde was added thereto. After the mixture was stirred for 30 minutes, 20 mL of water was added thereto, and the mixture was cooled to room temperature. The mixture was stirred for one hour, and then the suspension was suction filtered using a 55-mm Nutsche filter. A solid thus obtained was purified by silica gel column chromatography (eluent: ethyl acetate/hexane=1:1→ethyl acetate/hexane 4:1), and thus 2.0 g of (E)-1-(2-amino-5-bromophenyl)-3-(pyridin-2-yl)prop-2-en-1-one was obtained (yield 71%).

$^1$H-NMR (CDCl$_3$) δ value: 6.43 (2H, broad-s), 6.61 (1H, d, J=8.8 Hz), 7.31 (1H, ddd, J=1.2 Hz, 4.8 Hz, 7.6 Hz), 7.36 (1H, dd, 2.4 Hz, 8.8 Hz), 7.48 (1H, d, J=7.6 Hz), 7.72 (1H, d, J=15.0 Hz), 7.75 (1H, ddd, 2.0 Hz, 7.6 Hz, 7.6 Hz), 8.07 (1H, d, J=2.4 Hz), 8.11 (1H, d, J=15.0 Hz), 8.71 (1H, broad-d, J=4.8 Hz) ppm.

Example 1

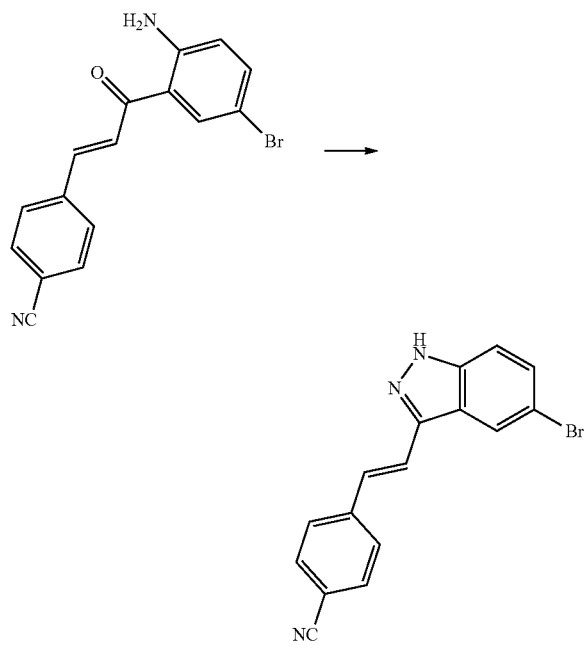

100 g of (E)-4(3-(2-amino-5-bromophenyl)-3-oxoprop-1-en-1-yl)benzonitrile obtained in Reference Example 1 was suspended in a liquid mixture of 1 L of acetic acid and 400 mL of a 3 mol/L aqueous solution of hydrochloric acid. To a mixture thus obtained, 62.1 g of an aqueous solution of sodium nitrite prepared from 22.1 g of sodium nitrite and 40 mL of water was added dropwise, while the internal temperature was maintained at or below 5° C. To a light yellow suspension produced after stirring for 30 minutes, 0.92 g of urea was added. The mixture was stirred for another 15 minutes, and then 59.2 g of L-ascorbic acid was added thereto. After the addition of L-ascorbic acid, the internal temperature was raised to the range of 70° C. to 80° C. for 2 hours, and the mixture was stirred for one hour. The mixture was cooled to 40° C., and then an aqueous solution of sodium hydroxide prepared from 500 mL of water and 48.9 g of sodium hydroxide was added dropwise thereto for 20 minutes. A suspension thus produced was added to 1.5 L of water, the mixture was stirred for 30 minutes at 20° C., and then crystals were suction filtered using a Nutsche filter having a diameter of 150 mm. The crystals were washed continuously with 1 L of water and then dried for 17 hours in a fan dryer at 60° C. Subsequently, 89 g of (E)-4-(2-(5-bromo-1H-indazol-3-yl)vinyl)benzonitrile was obtained as pale yellow crystals (yield 90%).

$^1$H-NMR (DMSO-d6) δ value:
7.51 (1H, dd, J=1.2 Hz, 8.4 Hz), 7.53 (1H, d, J=8.4 Hz), 7.54 (1H, d, J=16.8 Hz), 7.80 (2H, d, J=8.4 Hz), 7.90 (2H, d, J=8.4 Hz), 8.43 (1H, d, J=1.2 Hz), 13.54 (1H, s) ppm.

Example 2

Sodium Ascorbate 1.0 g of (E)-4(3-(2-amino-5-bromophenyl)-3-oxoprop-1-en-1-yl)benzonitrile obtained in Reference Example 1 was suspended in a liquid mixture of 10 mL of acetic acid and 4 mL of a 3 mol/L aqueous solution of hydrochloric acid. To a mixture thus obtained, an aqueous solution of sodium nitrite prepared from 0.22 g of sodium nitrite and 0.4 mL of water was added dropwise while the internal temperature was maintained at 5° C. or lower. To a light yellow suspension produced after stirring for 30 minutes, 0.76 g of sodium L-ascorbate was added. After the addition of sodium L-ascorbate, the internal temperature was raised to the range of 70° C. to 80° C. for one hour, and the mixture was stirred for another 30 minutes. The mixture was cooled to 40° C., and then an aqueous solution of sodium hydroxide prepared from 5 mL of water and 0.49 g of sodium hydroxide was added. A suspension thus produced was stirred for 30 minutes at 20° C., and then crystals were suction filtered using a Nutsche filter having a diameter of 55 mm. The crystals were washed continuously with 15 mL of water and then dried for 17 hours in a fan dryer at 60° C. Subsequently, 0.82 g of (E)-4-(2-(5-bromo-1H-indazol-3-yl)vinyl)benzonitrile was obtained as pale yellow crystals (yield 83%).

Example 3

Isoascorbic Acid

A reaction was carried out in the same manner as in Example 2, except that 0.67 g of isoascorbic acid was used instead of sodium L-ascorbate used in Example 2. As a result, 0.79 g of (E)-4-(2-(5-bromo-1H-indazol-3-yl)vinyl)benzonitrile was obtained (yield 80%).

Example 4

Ascorbic Acid Ester

A reaction was carried out in the same manner as in Example 2, except that 1.58 g of 6-O-palmitoyl-L-ascorbate was used instead of sodium L-ascorbate used in Example 2. As a result, 0.82 g of (E)-4-(2-(5-bromo-1H-indazol-3-yl)vinyl)benzonitrile was obtained (yield 83%).

Example 5

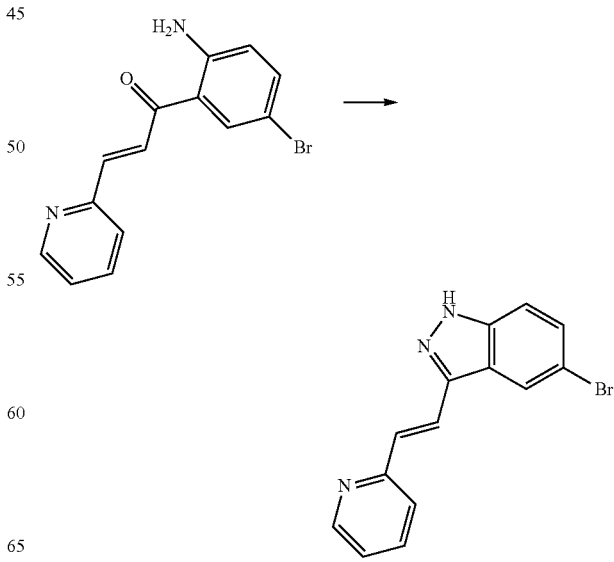

0.93 g of (E)-1-(2-amino-5-bromophenyl)-3-(pyridin-2-yl)prop-2-en-1-one obtained in Reference Example 2 was suspended in a liquid mixture of 10 mL of acetic acid and 4 mL of a 3 mol/L aqueous solution of hydrochloric acid. To a mixture thus obtained, an aqueous solution of sodium nitrite prepared from 0.22 g of sodium nitrite and 0.4 mL of water was added dropwise, while the internal temperature was maintained at or below 5° C. To a dark brown solution produced after stirring for 30 minutes, 0.67 g of sodium L-ascorbate was added. After the addition of L-ascorbic acid, the internal temperature was raised to the range of 70° C. to 80° C. for one hour, and the mixture was stirred for another 30 minutes. The mixture was cooled to 40° C., and then an aqueous solution of sodium hydroxide prepared from 20 mL of water and 0.49 g of sodium hydroxide was added. The reaction liquid was further stirred for 30 minutes at 20° C., and then 20 mL of ethyl acetate was added thereto. A lower layer (aqueous layer) was separated, and then the upper layer (organic layer) was concentrated under reduced pressure. Thus, a crude product was obtained. This crude product was purified by silica gel column chromatography (eluent: ethyl acetate/hexane=2:1→ethyl acetate/hexane 4:1), and thus 0.52 g of (E)-5-bromo-3-(2-(pyridin-2-yl)vinyl)-1H-indazole was obtained as orange-colored crystals (yield 56%).

$^1$H-NMR (DMSO-d6) δ value:

7.28 (1H, ddd, J=1.2 Hz, 4.8 Hz, 7.6 Hz), 7.53 (1H, dd, J=1.6 Hz, 8.8 Hz), 7.57 (1H, d, J=8.8 Hz), 7.59 (1H, d, J=16.4 Hz), 7.72 (1H, d, J=7.6 Hz), 7.82 (1H, ddd, J=2.0 Hz, 7.6 Hz, 7.6 Hz), 7.95 (1H, d, J=16.4 Hz), 8.45 (1H, broad-s), 8.61 (1H, broad-d, J=4.8 Hz), 13.48 (1H, s) ppm.

Comparative Example 1

Tert-Butylhydroquinone

A reaction was carried out in the same manner as in Example 2, except that 0.64 g of tert-butylhydroquinone was used instead of sodium L-ascorbate used in Example 2. As a result, (E)-4-(2-(5-bromo-1H-indazol-3-yl)vinyl)benzonitrile could not be obtained.

Comparative Example 2

Ascorbic Acid Diester

A reaction was carried out in the same manner as in Example 2, except that 2.50 g of 2,6-di-O-palmitoyl-L-ascorbate was used instead of sodium L-ascorbate used in Example 2. As a result, (E)-4-(2-(5-bromo-1H-indazol-3-yl)vinyl)benzonitrile could not be obtained.

Comparative Example 3

Ascorbic Acid Diester

A reaction was carried out in the same manner as in Example 2, except that tin dichloride monohydrate was used instead of sodium L-ascorbate used in Example 2. As a result, (E)-4-(2-(5-bromo-1H-indazol-3-yl)vinyl)benzonitrile was obtained (yield 58%).

Comparative Example 4

Ascorbic Acid Diester

A reaction was carried out in the same manner as in Example 5, except that tin dichloride monohydrate was used instead of L-ascorbic acid used in Example 5. As a result, (E)-5-bromo-3-(2-(pyridin-2-yl)vinyl)-1H-indazole was obtained (yield 15%).

An indazole compound produced by the method for producing an indazole compound according to the embodiment of the invention is useful as a synthetic intermediate of a medicinal drug, an agrochemical, or a functional material.

What is claimed is:

1. A method for producing an indazole compound, comprising obtaining an indazole compound represented by the following General Formula (3) or a salt thereof from a diazonium salt prepared from an aniline compound represented by the following General Formula (2) in the presence of a compound represented by the following General Formula (1),

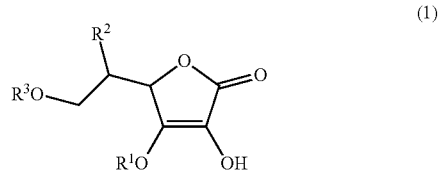

in the formula, $R^1$ represents a hydrogen atom or an alkali metal;

$R^2$ represents a hydrogen atom, a hydroxyl group, an amino group, a mercapto group, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{1-6}$ alkoxy group which may have a substituent, a $C_{6-20}$ aryloxy group which may have a substituent, a $C_{1-6}$ alkylamino group which may have a substituent, a $C_{6-20}$ arylamino group which may have a substituent, a $C_{1-6}$ alkylthio group which may have a substituent, a $C_{6-20}$ arylthio group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent; and $R^3$ represents a hydrogen atom, a $C_{1-30}$ alkylcarbonyl group which may have a substituent, or a $C_{6-20}$ arylcarbonyl group which may have a substituent,

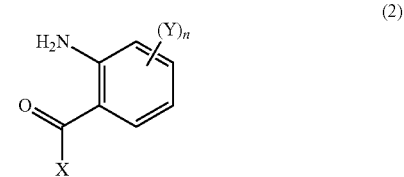

in the formula,

X represents a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{2-6}$ alkenyl group which may have a substituent, a $C_{2-6}$ alkynyl group which may have a substituent, a $C_{6-20}$ aryl group which may have a substituent, or a heterocyclic group which may have a substituent;

Y's each independently represent a halogen atom, a carboxyl group, a hydroxyl group, an amino group, a mercapto group, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{1-6}$ alkoxy group which may have a substituent, a $C_{6-20}$ aryloxy group which may have a substituent, a $C_{1-6}$ alkylamino group which may have a substituent, a $C_{6-20}$ arylamino group which may have a substituent, a $C_{1-6}$ alkylthio group which may have a substituent, a $C_{6-20}$ arylthio group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent; and n is an integer from 0 to 4; and in a case in which n is 2 or greater, a plurality of existing Y's may be identical with or different from one another, and

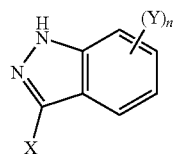

(3)

in the formula, X, Y, and n have the same meanings as those described above.

2. The method for producing an indazole compound according to claim 1, wherein the aniline compound represented by General Formula (2) is a compound represented by the following General Formula (4), and the indazole compound represented by General Formula (3) is a compound represented by the following General Formula (5),

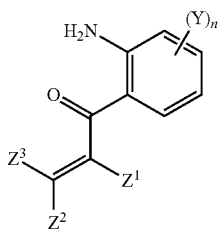

(4)

in the formula, $Z^1$ to $Z^3$ each independently represent a hydrogen atom, a $C_{1-6}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, a $C_{3-8}$ cycloalkenyl group which may have a substituent, a $C_{6-20}$ aryl group which may have a substituent, or a heterocyclic group which may have a substituent;

$Z^1$ and $Z^2$ may be bonded together to form a ring; and

Y and n have the same meanings as those described above, and

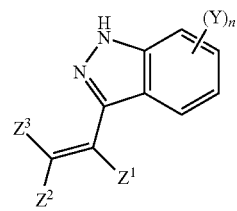

(5)

in the formula, $Z^1$ to $Z^3$, Y, and n have the same meanings as those described above.

3. The method for producing an indazole compound according to claim 1, wherein the aniline compound represented by General Formula (2) is a compound represented by the following General Formula (6), and the indazole compound represented by General Formula (3) is a compound represented by the following General Formula (7),

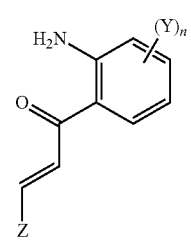

(6)

in the formula,

Z represents a hydrogen atom, a $C_{1-6}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, a $C_{3-8}$ cycloalkenyl group which may have a substituent, a $C_{6-20}$ aryl group which may have a substituent, or a heterocyclic group which may have a substituent; and Y and n have the same meanings as those described above, and

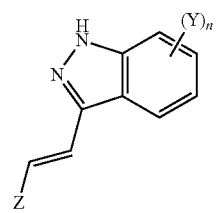

(7)

in the formula, Z, Y, and n have the same meanings as those described above.

4. The method for producing an indazole compound according to claim 3, wherein Z is a group represented by the following General Formula (8),

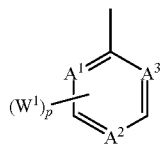
(8)

in the formula,

W¹ represents a halogen atom, a cyano group, a nitro group, an amino group, a formyl group, a carboxyl group, a sulfo group, a hydroxyl group, a $C_{1-6}$ alkylcarbonyl group which may have a substituent, a $C_{6-20}$ arylcarbonyl group which may have a substituent, a $C_{1-6}$ alkylsulfonyl group which may have a substituent, a $C_{6-20}$ arylsulfonyl group which may have a substituent, a $C_{1-6}$ alkylsulfinyl group which may have a substituent, a $C_{6-20}$ arylsulfinyl group which may have a substituent, a $C_{1-6}$ alkylamino group which may have a substituent, a $C_{6-20}$ arylamino group which may have a substituent, a $C_{1-6}$ alkoxy group which may have a substituent, a $C_{6-20}$ aryloxy group which may have a substituent, a $C_{1-6}$ alkyl group which may have a substituent, a $C_{3-8}$ cycloalkyl group which may have a substituent, a $C_{1-6}$ alkoxy-$C_{1-6}$ alkyl group which may have a substituent, a $C_{6-20}$ aryl-$C_{1-6}$ alkyl group which may have a substituent, a $C_{2-6}$ alkenyl group which may have a substituent, a $C_{3-8}$ cycloalkenyl group which may have a substituent, a $C_{2-6}$ alkynyl group which may have a substituent, a $C_{6-20}$ aryl group which may have a substituent, or a heterocyclic group which may have a substituent;

$A^1$ to $A^3$ each independently represent —$CR^4$— or —N—;

$R^4$ represents a hydrogen atom or $W^1$;

p is an integer from 0 to 5; in a case in which p is 2 or greater, a plurality of existing $W^1$'s may be identical with or different from one another; and two or more $W^1$'s may be bonded together to form a fused ring together with a benzene ring.

5. The method for producing an indazole compound according to claim 4, wherein $W^1$ represents a halogen atom, a cyano group, a nitro group, a formyl group, a carboxyl group, a sulfo group, a $C_{1-6}$ alkylcarbonyl group which may have a substituent, a $C_{6-20}$ arylcarbonyl group which may have a substituent, a $C_{1-6}$ alkylsulfonyl group which may have a substituent, a $C_{6-20}$ arylsulfonyl group which may have a substituent, a $C_{1-6}$ alkylsulfinyl group which may have a substituent, or a $C_{6-20}$ arylsulfinyl group which may have a substituent; and p is 1.

6. The method for producing an indazole compound according to claim 1, wherein the diazonium salt prepared from the aniline compound is a diazonium salt obtained by causing nitrite to act on the aniline compound under acidic conditions.

7. The method for producing an indazole compound according to claim 1, wherein a solvent used in the process of obtaining the diazonium salt is a mixed solvent including acetic acid and water.

8. The method for producing an indazole compound according to claim 1, wherein Y represents a halogen atom, a mercapto group, a $C_{1-6}$ alkylthio group which may have a substituent, a $C_{1-6}$ alkyl group which may have a substituent, a $C_{1-6}$ alkoxy group which may have a substituent, a carboxyl group, a $C_{3-8}$ cycloalkenyl group which may have a substituent, a $C_{6-20}$ aryl group which may have a substituent, or a heterocyclic group which may have a substituent.

9. The method for producing an indazole compound according to claim 1, wherein Y represents a halogen atom, a $C_{3-8}$ cycloalkenyl group which may have a substituent, a $C_{6-20}$ aryl group which may have a substituent, or a heterocyclic group which may have a substituent.

10. The method for producing an indazole compound according to claim 1, wherein $R^2$ represents a hydroxyl group.

11. The method for producing an indazole compound according to claim 1, wherein the compound represented by General Formula (1) is a compound represented by the following General Formula (10),

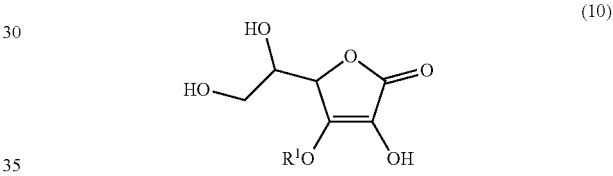
(10)

in the formula, $R^1$ has the same meaning as that described above.

12. The method for producing an indazole compound according to claim 1, wherein the compound represented by General Formula (1) is a compound represented by the following General Formula (11),

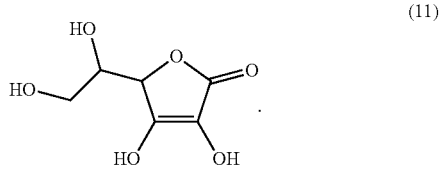
(11)

* * * * *